United States Patent

Marek et al.

[11] Patent Number: 5,972,912
[45] Date of Patent: Oct. 26, 1999

[54] METHOD FOR LYOPHILIZING IFOSFAMIDE

[75] Inventors: Michael J. Marek; Garnet G. Smith; Thomas R. Kovalcik, all of Albuquerque, N.Mex.

[73] Assignee: S.P. Pharmaceuticals, Albuquerque, N.Mex.

[21] Appl. No.: 09/213,635

[22] Filed: Dec. 17, 1998

[51] Int. Cl.[6] .............................. C07F 9/547; C07F 9/576
[52] U.S. Cl. .................... 514/105; 514/79; 558/81; 544/1
[58] Field of Search .................... 558/81; 544/1

[56] References Cited

U.S. PATENT DOCUMENTS

| | | | |
|---|---|---|---|
| 3,732,340 | 5/1973 | Arnold et al. | 260/936 |
| 4,537,883 | 8/1985 | Alexander et al. | 514/110 |
| 4,777,043 | 10/1988 | Bennett et al. | 514/561 |
| 4,882,452 | 11/1989 | Engel et al. | 558/81 |
| 5,204,335 | 4/1993 | Sauerbier et al. | 514/105 |
| 5,227,373 | 7/1993 | Alexander et al. | 514/110 |

OTHER PUBLICATIONS

Effects of Excipients on the Crystallization of Pharmaceutical Compounds During Lyophilization, Korey, D.J., J. Parenter. Science Technology, 43, 2 (1989).

Characterization of the Sucrose/Glycine/Water System by Differential Scanning Calorimetry and Freeze–Drying Microscope, Kasraian, K., et al., Pharaceutical Development and Technology 3(2) 233–239 (1988).

*Primary Examiner*—Mukund J. Shah
*Assistant Examiner*—Pavanaram K Sripada
*Attorney, Agent, or Firm*—Daniel F. Perez; Gardere & Wynne, L.L.P.

[57] ABSTRACT

A method of lyophilizing an oxazaphosphorin and a preparation produced thereby including dissolving an oxazaphosphorin in water, adding an amino acid to a molar ratio of between 1 to 10 amino acid to 1 oxazaphosphorin to produce a mixture and lyophilizing said mixture to remove said water, is disclosed.

41 Claims, 2 Drawing Sheets

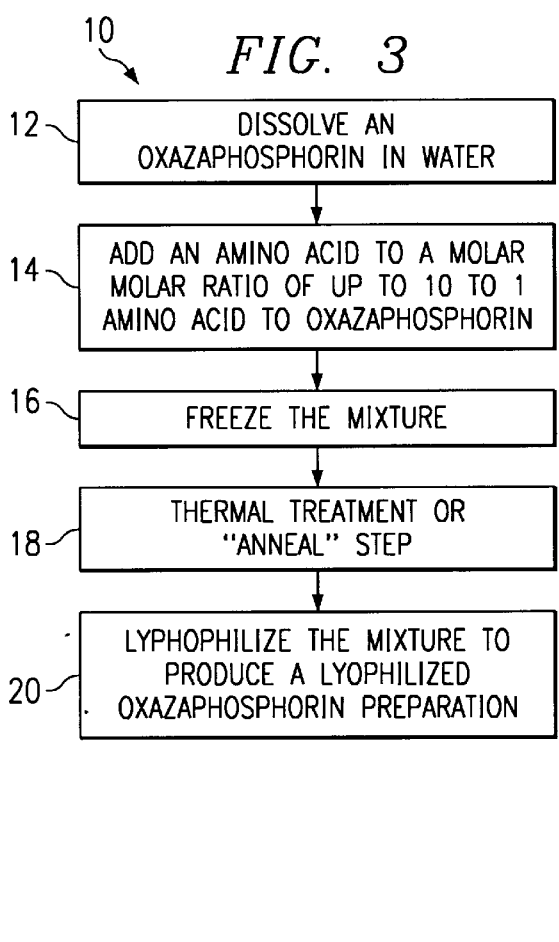
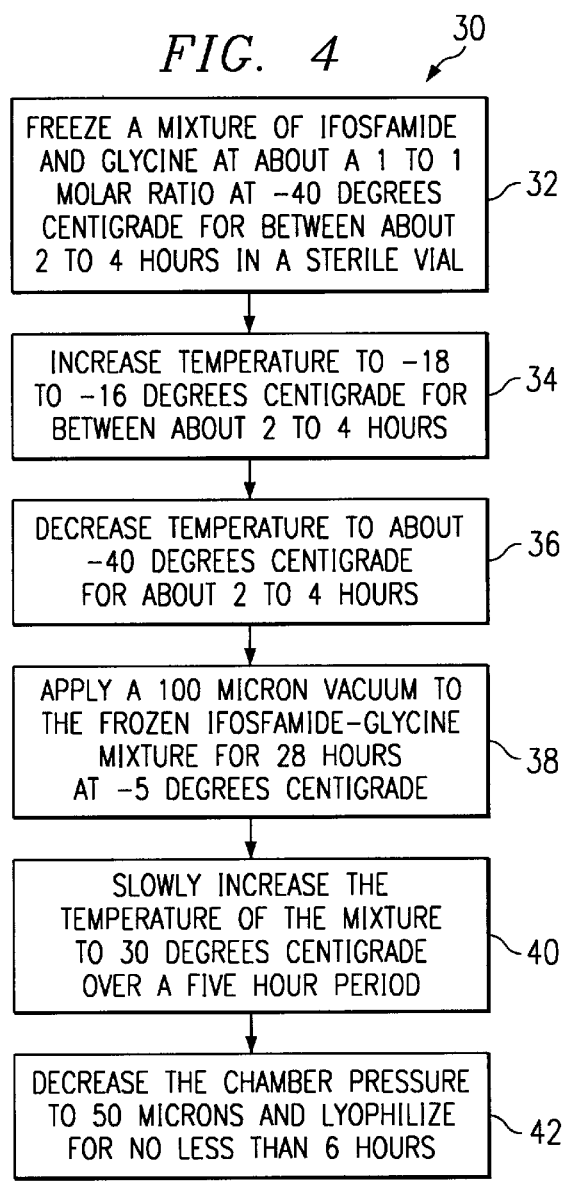

METHOD FOR LYOPHILIZING IFOSFAMIDE

TECHNICAL FIELD OF THE INVENTION

The present invention relates to a process for lyophilizing labile compounds that can have low melting points, are hygroscopic and can sinter, forming lumps that are poorly miscible in water or become electrostatically charged at low storage temperatures, and more particularly, to a process for lyophilizing ifosfamide and ifosfamide-related compounds having improved stability and shelf-life.

BACKGROUND OF THE INVENTION

Without limiting the scope of the invention, its background is described in connection with the preparation of ifosfamide preparations for use in human therapy.

Heretofore, in this field, the preparation and long term storage of labile hygroscopic compounds, such as ifosfamide, has been difficult. Ifosfamide is a chemotherapeutic agent chemically related to the nitrogen mustards and synthetic analogs of cyclophosphamide. Ifosfamide is 3-(2-chloroethyl)-2-[(chloroethyl amino)] tetrahydro-2H-1, 3, 2-oxazaphosphorin 2-oxide, and has a molecular formula of $C_7H_{15}Cl_2N_2O_2P$ and its molecular weight is 261.1 Daltons.

When first synthesized, ifosfamide is a white crystalline powder that is somewhat soluble in water, however, as the composition is stored, it tends to change to a yellowish color. Ifosfamide belongs to a group of chemical compounds denoted oxazaphosphorins, which are presently in use as therapeutic agents for the treatment of tumors. In particular, ifosfamide is presently used in combination with certain other antineoplastic agents, and is a third line chemotherapeutic for the treatment of testicular cancers derived from germ cells. Generally, it is used in conjunction with a hemorrhagic prophylactic agent, such as mesna.

The lack of stability in water, and its hygroscopic nature, have proven practical challenges to the preparation, processing and long term storage of ifosfamide and its derivatives. In particular, problems with the accuracy of the amount dispensed occur when ifosfamide is prepared for storage as a dried powder. For example, dispensing the dried powder leads to inaccuracies in the amount dispensed and the dosage of ifosfamide when reconstituted and used for treatment. Dispensing the powdered form of ifosfamide into vials for storage also increases the likelihood that microbial contaminants may be introduced during the filling process.

Furthermore, even in the powdered form, ifosfamide suffers from sensitivity to light and heat. The lack of stability of crystallized and reconstituted forms of ifosfamide greatly affect the dosage accuracy during use. The instability of ifosfamide and other oxazaphosphorins has led to the need to find methods for long term storage of these compounds.

One approach to the problem was described in U.S. Pat. No. 5,204,335, entitled "Ifosfamide Lyophilizate and Process for Its Preparation," issued to Sauerbier, et al. Briefly, a lyophilizate is produced by freezing and drying an aqueous or aqueous/alcoholic (preferably aqueous/ethanolic) solution of ifosfamide and a hexitol. The process disclosed involved the use of a hexitol such as, for example, mannitol, to produce an ifosfamide lyophilizate.

SUMMARY OF THE INVENTION

The present inventors have discovered that current formulations of ifosfamide fail to have the longevity and stability required for long term storage of compounds in the oxazaphosphorin chemical group. For example, ifosfamide is presently available commercially as a dried powder formulation. The dried formulation is purified out of crystals aseptically precipitated, dried and powder-filled, an inherently complex and difficult process. Therefore, a need has arisen for a lyophilized formulation that can be filled into vials in the liquid state rather than as a powder, thereby increasing the accuracy of the dose and decreasing the potential for the introduction of microbial contamination.

More particularly, the present invention is directed to a method and composition for lyophilizing an oxazaphosphorin in water by dissolving the oxazaphosphorin in water and adding an amino acid to a molar ratio of between about 1.0 and 10 to 1, amino acid to oxazaphosphorin, for example, glycine to ifosfamide. A weight to weight ratio may be between about 0.3 to 3 to 1, amino acid to oxazaphosphorin, for example, glycine to ifosfamide.

The amino acid-oxazaphosphorin produce a mixture that is then lyophilized to remove the water. The lyophilized mixture is a stable preparation that can be stored long-term, eliminates the potential contamination inherent to powder filling and improves the dosage reliability.

In one embodiment of the invention, the method for lyophilizing an oxazaphosphorin includes the steps of; mixing 0.3 to 3 parts by weight of an amino acid selected from the group consisting of glycine, lysine, alanine, serine and arginine for each part by weight of compounds of the chemical group oxazaphosphorins. The mixture may then be frozen to about −40 degrees Centigrade and held at that temperature for 2 to 4 hours. Next, the temperature of the frozen mixture is increased to between about −18 to −16 degrees Centigrade and the temperature is held for about 2 to 4 hours. The temperature may then be decreased to about −40 degrees Centigrade and held for about 2 to 4 hours. Non-adsorptively bound water may be removed by sublimation at a temperature between about −30 and −5 degrees Centigrade and a pressure between 100 and 300 $\mu$m Hg for a minimum of 24 hours. Adsorptively bound water may be removed at a temperature of about 30 degrees Centigrade and a pressure less than 100 $\mu$m Hg for a minimum of about 6 hours.

The oxazaphosphorin may be dissolved in water to a ratio of up to 10% weight to volume and may be in a pharmaceutically acceptable carrier. More specifically, the ratio of oxazaphosphorin to amino acid may be glycine and oxazaphosphorin, having a weight ratio of 0.3 glycine to 1 ifosfamide, to about 1 glycine to 1 ifosfamide and may even be about 3 glycine to 1 ifosfamide. The amino acid may be a small aliphatic amino acid selected from the group consisting of glycine, alanine, serine, arginine or lysine. In one embodiment the amino acid is glycine.

Yet another embodiment of the present invention is a lyophilized preparation including, an oxazaphosphorin and an amino acid at a 1–10 molar ratio with the oxazaphosphorin. The oxazaphosphorin-amino acid mixture may be lyophilized as described herein.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 3 is a flow diagram of the basic steps for preparing a lyophilized compound according to the present invention; and FIG. 4 is a flow diagram of a lyophilization protocol for use with the present invention.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Oxazaphosphorins, such as ifosfamide, are highly hygroscopic compounds that generally dissolve in water. The solubility of these compounds, however, is limited to about 10 percent by weight, as is the case for ifosfamide. Once dissolved in water, for example, ifosfamide is only stable for a limited period of time. Ifosfamide is only stable for about three to four hours at room temperature or thirty-six hours at 4 to 6 degrees centigrade, causing its effective dosage to vary greatly with time.

The present inventors have determined that one problem with freeze drying compounds like ifosfamide, is the somewhat oily consistency of the compound when present as a solid. This oily consistency causes the lyophilizate to collapse during freeze drying, which leads to a slush-like preparation that is difficult to dissolve when rehydrated. In contrast to present methods, the ifosfamide lyophilizate prepared according to the present invention displays neither discoloration, nor any change in the consistency of the freeze dried ifosfamide under common storage conditions. Furthermore, because the ifosfamide is not packaged as a dry powder, but rather is dispensed into the storage vial as a liquid ifosfamide solution prior to lyophilization, the accuracy of the amount stored is increased. By increasing the accuracy of the effective dose of ifosfamide stored in a vial, consistency in the treatment regimen can also be increased. The present invention produces a freeze dried ifosfamide solid with increased crystallinity that displays optimal solubility properties after long term storage. Thermal treatment of the frozen mixture provides increased crystallinity and stability in the final freeze-dried preparation. The analysis of the thermal treatment or annealing step to determine the temperature of the mixture may be conducted using, e.g., differential scanning calorimetry.

Figure 1:
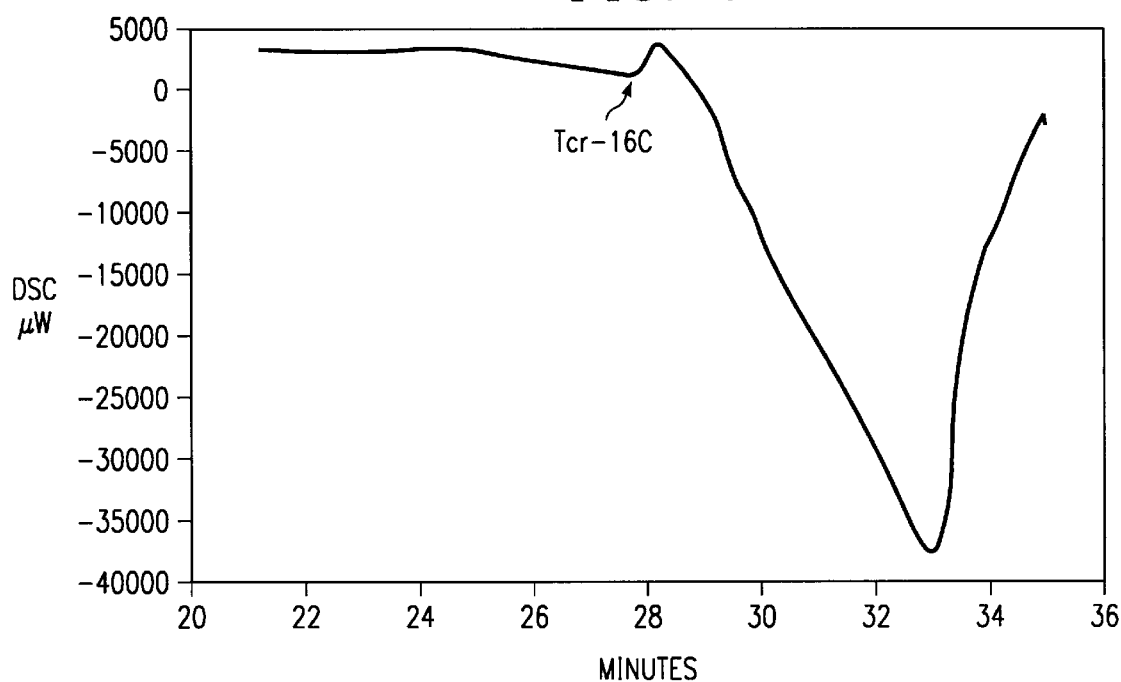
FIG. 1 is a differential scanning calorimetry warming thermogram depicting exotherm of glycine and ifosfamide according to the present invention.

FIG. 1 depicts the differential scanning calorimetry (DSC) thermogram of an ifosfamide glycine mixture. The cooling and warming of an ifosfamide:glycine mixture at a 1 to 1.05 molar ratio is depicted. A crystallization exotherm is observed at −16 degrees Centigrade.

Figure 2:
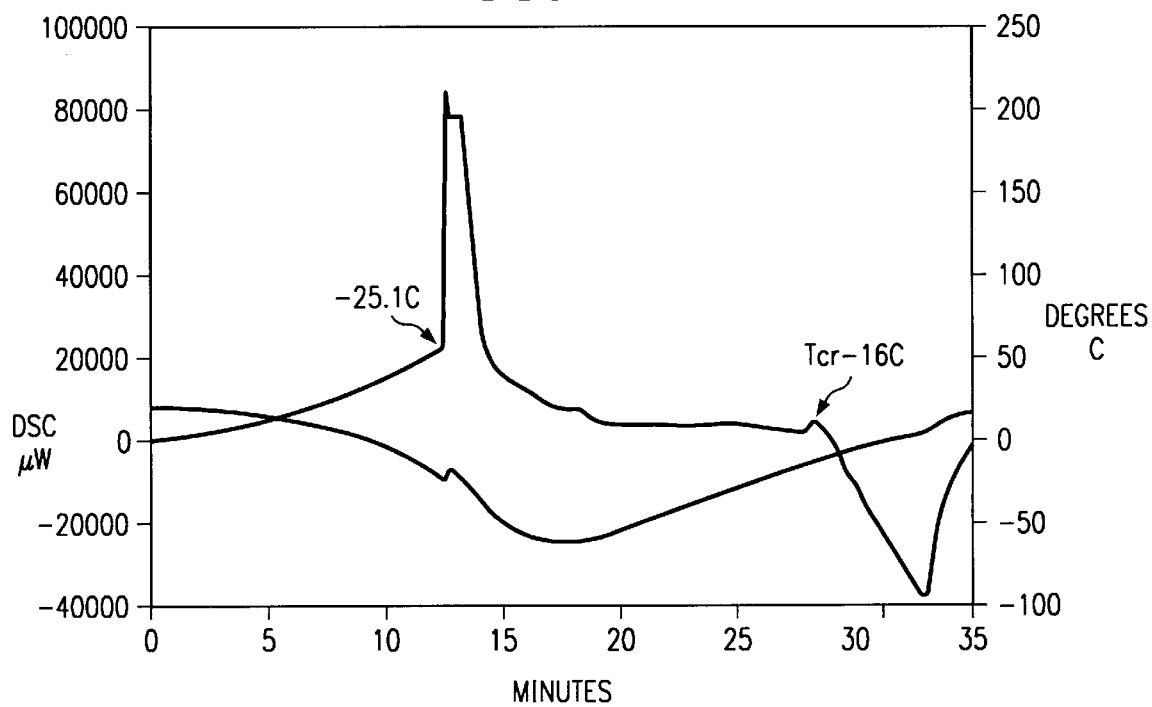
FIG. 2 is another differential scanning calorimetry graph of the cooling and warming of one embodiment according to the present invention.

FIG. 2 shows super cooling of the ifosfamide glycine amorphous matrix. The differential scanning calorimetry thermogram shows the cooling and warming of a ifosfamide:glycine mixture at a 1 to 1.05 molar ratio. Supercooling at −25° C. and a crystallization exotherm for glycine at −16° C. was found.

The present invention reduces the sensitivity to atmospheric moisture commonly encountered with dry filled ifosfamide crystals. The present invention also reduces the potential for the introduction of micro-contaminants during the manufacturing process.

More particularly, the present invention is a lyophilized preparation or product and method for stabilizing ifosfamide derivatives in a lyophilized form. FIG. 3 is a flow diagram 10 of the basic steps involved in preparing a oxazaphosphorin lyophilizate. In step 12, ifosfamide is dissolved in water. The oxazaphosphorin may be dissolved in water up to 10 percent weight per volume. Also, the pH of the solution may be adjusted. The pH of the ifosfamide-amino acid solution can be between about a pH of 4 and a pH of 7. When using glycine as the amino acid, the glycine can serve as a pH buffer for the solution. Next, in step 14, an amino acid is added to stabilize the oxazaphosphorin for lyophilization. The molar ratio of amino acid to ifosfamide will generally be between 1 to 10 amino acid to 1 ifosfamide. Alternatively, a weight to weight ratio may be used.

The mixture may then be frozen at, e.g., −40 degrees Centigrade in step 18. The frozen mixture is then thermally treated by increasing the temperature to −16 degrees Centigrade and held 2 to 4 hours to provide increased crystallization of the frozen matrix. In step 18, the frozen mixture is thermally treated or "annealed". Finally, in step 20, the oxazaphosphorin-amino acid mixture, is lyophilized to prepare a stable oxazaphosphorin containing lyophilizate for use in patients.

Amino acids for use as stabilizers during the lyophilization process of, e.g., ifosfamide will generally include glycine, serine, alanine, lysine and arginine. The amino acids will generally be the left-handed chiral forms of the amino acid. The molar ratio of the amino acid to ifosfamide can be between about 1 to 1 to 10 to 1. The amino acids should be as pyrogen free as possible and should meet sterility, pyrogenicity, general safety and purity standards as required by FDA Office of Drug standards. Likewise, the ifosfamide, buffering solutions (if any), and any carrier also included in solution prior to lyophilization will generally meet these standards when prepared for animal or human use.

In one embodiment the molar ratio of glycine to ifosfamide is 1 to 1. The molar ratio may be varied to optimize the relative solubility of ifosfamide and the amino acid, and the efficiency and stability of the solution during lyophilization.

For example, when the amino acid is the glycine-buffered ifosfamide solution may be filter sterilized, using for example, a 0.22 micron filter. The sterilized glycine-ifosfamide solution may be dispensed into presterilized glass vials immediately upon sterilization.

FIG. 4, is a flow diagram of a method of lyophilizing ifosfamide and is generally designated as 30. In step 32, a mixture of ifosfamide at a 1 to 1.5–1.1 molar ratio with glycine is frozen to about −30 and −70 degrees Centigrade for 2 to 4 hours. Preferably, a temperature of −40 degrees Centigrade is used in step 32. The ifosfamide-glycine mixture may be dispensed as a sterile solution prior to freezing step 32. Sterile vials may be directly lyophilized in a controlled temperature vacuum chamber. The glass vials may be sterilized using techniques known to those of ordinary skill in the art. Next, in step 34, the temperature of the mixture is increased to between about −18 to −16 degrees Centigrade for about 2 to 4 hours. Next, the temperature is further decreased to about −40 degrees Centigrade for about 2 to 4 hours, in step 36. In step 38, a vacuum of about 100 microns is placed on the mixture for about 24 to 28 hours, from between about −35 to −5 degrees Centigrade to remove non-adsorptively bound water. Following the primary drying period, the temperature of the chamber in which the vials are located is increased to between 20 and 30 degrees Centigrade, initiating a drying period for a minimum of 6 hours to remove adsorptively bound water, as shown in step 40. The temperature will generally be increased gradually, or may be increased in one step or in a number of steps. Also, the vacuum of the chamber can be increased to 50 microns. Finally in step 42, when the chamber pressure reaches about 50 microns, the lyophilization continues for another 3 hours, resulting in residual water content of less than 0.5%.

The glass vials may be sterilized using techniques known to those of ordinary skill in the art. Vials may be loaded onto a lyophilizing stand, rack or in a freeze drying chamber. The glass vials may be frozen to between about −30 and −70 degrees Centigrade for two hours.

In one embodiment, the shelf temperature of the vials having the ifosfamide-glycine mixture is decreased to about −45 degrees Centigrade. The temperature is slowly increased to −5 degrees over a period of about 3 hours. Alternatively, the ifosfamide glycine solution may be brought down to −35 degrees Centigrade for about four hours. Either of these methods ensure freezing.

Lyophilization of the solution commences by evacuating the freeze drying chamber or the individual vials with the shelf temperature at −5 degrees (if the vials are on a freeze drying stand or rack). The pressure within the vial is decreased to about 100 microns. The 100 micron vacuum freeze process is conducted from between about 28 to 36 hours, depending on the volume of the solution. Next, the pressure in the vial is decreased to about 50 microns and the lyophilizate temperature is increased to 30 degrees Centigrade for a minimum of 6 hours.

EXAMPLE

The following mixture of ifosfamide and glycine was prepared as a prelyophilization solution.

| | |
|---|---|
| Ifosfamide | 80 mg/mL |
| Glycine | 24 mg/mL |
| pH | 6.1 |

A glass vessel is filled with 90% water for injection and ifosfamide is added with stirring to complete dissolution. Glycine is added with stirring. The solution is then made up to the final volume and the pH measured.

Following sterile filtration, 12.5 mL aliquots were filled in 20 cc vials. Lyophilization was then carried out as follows:

1. The vials were placed into the lyophilizer and frozen to −40° C. (shelf temperature) for 4 hours.
2. The shelf temperature was then raised to −16° C. and held for 2 hours, as the annealing step.
3. The shelf temperature was then decreased to −40° C. and held for 3 hours.
4. Vacuum was applied (chamber pressure of 100 μm Hg)and the shelf temperature increase to −22° C. at 10°/hr and held for 1 hour.
5. The shelf temperature was then raised to −5° C. at 10°/hr and held for a minimum of 24 hours and the product thermocouples have met or exceeded the shelf temperature.
6. The shelf temperature was then raised to 30° C. at 10°/hr and the chamber pressure lowered to 50 μm and held a minimum of 6 hours.
7. The chamber was then backfilled to 11 PSI and the vials stoppered.
8. The chamber pressure was allowed to come to ambient and the vials removed from the lyophilizer.
9. The residual moisture by Karl Fisher analysis is less than 0.5%.

| Quality of Ifosfamide Formulation Containing Molar excess of Glycine Excipient | | | |
|---|---|---|---|
| Glycine Molar Concentration | Ifosfamide Molar Concentration | Molar Ratio Glycine:Ifosfamide | Cake Appearance |
| 0.06M | 0.3M | 0.2:1 | no cake, shrunken yellow mass |
| 0.12M | 0.3M | 0.4:1 | very shrunken yellow cake |
| 0.24M | 0.3M | 0.8:1 | shrunken cake, off white |
| 0.32M | 03.M | 1.05:1 | white cake approx. Fill volume |
| 0.80M | 0.2M | 4.0:1 | white cake approx. fill volume |

Glass vials for use with the present invention will be presterilized and made of, e.g., tubular or molded glass. When shaped to include a rubber stopper or flanged cap, for example, the glass vial and any stopper can generally be sterilized during manufacture. The size of the vial selected will vary with the dosage requirements and the volume necessary to reconstitute the lyophilizate.

The amount of solution dispensed into a vial prior to lyophilization will vary depending on the dosage and amount necessary to treat a patient taking into consideration dosage and short term stability requirements. For example, the amount may vary depending on the weight to volume of ifosfamide in solution, the size of the vial, and the dosage requirements. For example, a 4 percent solution of ifosfamide may be lyophilized and then reconstituted to a concentration such that a 3.3 to 5.0 grams solution per meter squared per day may be injected into a patient. A single vial dosage of ifosfamide may be varied from 100 milligrams to 10 grams. Larger volumes and amounts of ifosfamide may be lyophilized according to the present invention.

One dosage of ifosfamide may be dissolved in a 5 milliliters isotonic NaCl solution and added to 1000 milliliters of intravenous fluid (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for preparing a lyophilized oxazaphosphorin composition comprising the steps of:

adding an amino acid in a ratio of between 1 and 10 parts amino acid to 1 part oxazaphosporin in water to produce a mixture; and lyophilizing said mixture to remove said water.

2. The method of claim 1, wherein said oxazaphosphorin is dissolved in water to a ratio of up to 10% weight to volume.

3. The method of claim 1, further comprising the step of reconstituting said oxazaphosphorin composition in a pharmaceutically acceptable carrier.

4. The method of claim 1, wherein said ratio is a molar ratio of oxazaphosphorin to amino acid and ranges from between about 1 to 1 to about 1 to 10.

5. The method of claim 4, wherein said molar ratio of oxazaphosphorin to amino acid is about 1 to 1.

6. The method of claim 4, wherein said molar ratio of oxazaphosphorin to amino acid is about 1 to 1.1.

7. The method of claim 4, wherein said molar ratio of oxazaphosphorin to amino acid is about 1 to 4.

8. The method of claim 1, wherein said ratio is a weight to weight ratio and ranges from between about 1 to 0.3 oxazaphosphorin to amino acid to about 1 to 3 oxazaphosphorin to amino acid, weight to weight.

9. The method of claim 1, wherein said amino acid is selected from the group consisting of glycine, serine, alanine, arginine and lysine.

10. The method of claim 1, wherein said amino acid is glycine.

11. The method of claim 1, wherein said oxazaphosphorin is selected from the group consisting of ifosfamide and cyclophosphamide.

12. The method of claim 1, wherein the lyophilization of said mixture results in residual water content of less than 0.5 percent.

13. The method of claim 1, wherein the lyophilization process of said mixture includes a thermal treatment or annealing step.

14. The method of claim 13, wherein the thermal treatment or annealing step includes increasing the temperature to −18 to −16 degrees Centigrade for about 2 to 4 hours.

15. The method of claim 1, wherein the method provides a final preparation with increased crystallinity and stability.

16. The method of claim 1, wherein the step of lyophilizing said mixture comprises the steps of:
    freezing said mixture to about −40 degrees Centigrade and holding the frozen mixture at that temperature for 2 to 4 hours;
    increasing the temperature of the frozen mixture to between about −18 to −16 degrees Centigrade and holding the frozen mixture at this temperature for about 2 to 4 hours;
    decreasing the temperature to about −40 degrees Centigrade and holding the mixture at that temperature for about 2 to 4 hours;
    removing non-adsorptively bound water by sublimation by holding the mixture at a temperature between about −30 and −5 degrees Centigrade and a pressure between 100 and 300 μm Hg for a minimum of 24 hours; and
    removing adsorptively bound water by holding the mixture at a temperature of about 30 degrees Centigrade and a pressure less than 100 μm Hg for a minimum of 6 hours.

17. A method of making a freeze-dried lyophilized mixture comprising the steps of:
    mixing 0.3 to 3 parts by weight of an amino acid selected from the group consisting of glycine, serine, alanine, lysine, and arginine for each part by weight of compounds of the chemical group oxazaphophorins;
    freezing said mixture to about −40 degrees Centigrade and holding the frozen mixture at that temperature for 2 to 4 hours;
    increasing the temperature of the frozen mixture to between about −18 to −16 degrees Centigrade and holding the frozen mixture at this temperature for about 2 to 4 hours;
    decreasing the temperature to about −40 degrees Centigrade and holding the mixture at that temperature for about 2 to 4 hours;
    removing non-adsorptively bound water by sublimation by holding the mixture at a temperature between about −30 and −5 degrees Centigrade and a pressure between 100 and 300 μm Hg for a minimum of 24 hours; and
    removing adsorptively bound water by holding the mixture at a temperature of about 30 degrees Centigrade and a pressure less than 100 μm Hg for a minimum of 6 hours.

18. The method of claim 17, wherein said oxazaphosphorin is dissolved in water to a ratio of up to 10% weight to volume.

19. The method of claim 17, further comprising the step of reconstituting said freeze-dried lyophilized mixture in a pharmaceutically acceptable carrier.

20. The method of claim 17, wherein said ratio is a weight to weight ratio and ranges from between about 1 to 0.3 oxazaphosphorin to amino acid to about 1 to 3 oxazaphosphorin to amino acid, weight to weight.

21. The method of claim 17, wherein said amino acid is glycine.

22. The method of claim 17, wherein the steps of lyophilizing said mixture results in residual water content of less than 0.5 percent.

23. The method of claim 17, wherein the steps of lyophilizing said mixture includes a thermal treatment or annealing step at a temperature determined by thermal analysis of the mixture.

24. The method of claim 17, wherein the thermal treatment or annealing step entails increasing the temperature to −18 to −16 degrees Centigrade for about 2 to 4 hours.

25. The method of claim 17, wherein the methods provides a final preparation with increased crystallinity and stability.

26. A lyophilized preparation comprising:
    an oxazaphosphorin; and
    an amino acid having between a 1 and 10 molar ratio with said oxazaphosphorin.

27. The lyophilized preparation of claim 26, wherein said oxazaphosphorin is reconstituted in a pharmaceutically acceptable carrier.

28. The lyophilized preparation of claim 26, wherein said molar ratio of oxazaphosphorin to amino acid is about 1 to 1.1.

29. The lyophilized preparation of claim 26, wherein said amino acid is glycine.

30. The lyophilized preparation of claim 26, wherein said oxazaphosphorin is ifosfamide.

31. The lyophilized preparation of claim 26, wherein said oxazaphosphorin is cyclophosphamide.

32. A freeze dried formulation having improved stability and shelf-life comprising 0.3 to 3 parts by weight of an amino acid selected from the group consisting of glycine, serine, alanine, lysine, and arginine for each part by weight of compounds of the chemical group oxazaphosphorins.

33. The freeze-dried formulation of claim 32, wherein the amino acid is glycine.

34. The freeze-dried formulation of claim 32, wherein the oxazaphosphorin is ifosfamide.

35. A method of making a freeze-dried lyophilized mixture comprising the steps of:

mixing an amino acid selected from the group consisting of glycine, serine, alanine, lysine, and arginine in a ratio of between 1 and 10 parts of amino acid for each part of compounds of the chemical group oxazaphophorins;

freezing said mixture to about −40 degrees Centigrade and holding the frozen mixture at that temperature for 2 to 4 hours;

increasing the temperature of the frozen mixture to between about −18 to −16 degrees Centigrade and holding the frozen mixture at this temperature for about 2 to 4 hours;

decreasing the temperature to about −40 degrees Centigrade and holding the mixture at that temperature for about 2 to 4 hours;

removing non-adsorptively bound water by sublimation by holding the mixture at a temperature between about −30 and −5 degrees Centigrade and a pressure between 100 and 300 μm Hg for a minimum of 24 hours; and removing adsorptively bound water by holding the mixture at a temperature of about 30 degrees Centigrade and a pressure less than 100 μm Hg for a minimum of 6 hours.

36. The method of claim 35, wherein said ratio is a molar ratio of oxazaphosphorin to amino acid and ranges from about 1 to about 1.05.

37. The method of claim 35, wherein said ratio is a molar ratio of oxazaphosphorin to amino acid and ranges from about 1 to about 1.1.

38. The method of claim 35, wherein said ratio is a molar ratio of oxazaphosphorin to amino acid and ranges from about 1 to about 4.

39. A freeze-dried formulation having improved stability and shelf-life comprising between about 1 to 10 parts of an amino acid selected from the group consisting of glycine, serine, alanine, lysine, and arginine to one part by molar ratio of compounds of the chemical group oxazaphosphorins.

40. A method of preventing the formation of amorphous, non-crystalline material during the lyophilization of ifsofamide, comprising:

adding glycine to said ifosfamide in a molar ratio of between 1 and 4 glycine to 1 ifsofamide, to form a mixture; and annealing said mixture during lyophilization by raising the temperature of said mixture to about −16° C. and holding said mixture at that temperature for about two hours.

41. A lyophilized ifosfamide composition made by the process of claim 40.

* * * * *